(12) United States Patent
Huovie et al.

(10) Patent No.: US 9,284,237 B2
(45) Date of Patent: Mar. 15, 2016

(54) METHODS AND APPARATUSES FOR PROCESSING HYDROCARBONS

(71) Applicant: UOP LLC, Des Plaines, IL (US)

(72) Inventors: Chad R. Huovie, Park Ridge, IL (US); Charles P. Luebke, Mount Prospect, IL (US)

(73) Assignee: UOP LLC, Des Plaines, IL (US)

( * ) Notice: Subject to any disclaimer, the term of this patent is extended or adjusted under 35 U.S.C. 154(b) by 66 days.

(21) Appl. No.: 14/105,357

(22) Filed: Dec. 13, 2013

(65) Prior Publication Data

US 2015/0166437 A1    Jun. 18, 2015

(51) Int. Cl.
| | |
|---|---|
| C07C 7/12 | (2006.01) |
| C07C 5/03 | (2006.01) |
| C07C 41/09 | (2006.01) |
| C07C 43/04 | (2006.01) |
| C07C 2/12 | (2006.01) |
| C07C 5/41 | (2006.01) |
| C07C 7/148 | (2006.01) |

(52) U.S. Cl.
CPC ... *C07C 5/03* (2013.01); *C07C 2/12* (2013.01); *C07C 5/415* (2013.01); *C07C 7/14891* (2013.01); *C07C 41/09* (2013.01); *C07C 43/046* (2013.01); *C07C 2523/42* (2013.01); *C07C 2523/44* (2013.01); *C07C 2523/46* (2013.01); *C07C 2523/74* (2013.01); *C07C 2529/06* (2013.01)

(58) Field of Classification Search
CPC ........................................................ C07C 7/12
USPC ............... 585/315, 323, 456, 660, 906, 939; 568/939
See application file for complete search history.

(56) References Cited

U.S. PATENT DOCUMENTS

| | | |
|---|---|---|
| 3,193,489 A | 7/1965 | Gemmell |
| 3,763,034 A | 10/1973 | Kett et al. |
| 3,884,769 A | 5/1975 | Mikitenko et al. |
| 4,054,539 A | 10/1977 | Hensley, Jr. |

(Continued)

FOREIGN PATENT DOCUMENTS

| | | |
|---|---|---|
| WO | 2012033562 A1 | 3/2012 |
| WO | 2013013886 A2 | 1/2013 |

(Continued)

OTHER PUBLICATIONS

Helder, Y., "High-value products from catalytic cracking (fractions)/The C3 and C4," Pet. Tech. (ISSN 0152-5425) N.348 22-25 (Apr.-May 1989), n 348, p. 22-25, Apr. 1989; ISSN: 01525425, Publisher: Association Francaise des Techniciens et Professionnels du Petrole.

(Continued)

*Primary Examiner* — Kamal Saeed
*Assistant Examiner* — Janet L Coppins

(57) ABSTRACT

Methods and apparatuses for processing hydrocarbons are provided. In one embodiment, a method for processing hydrocarbons includes providing a stream of olefins including normal olefins and non-normal olefins. The method includes separating the normal olefins from the non-normal olefins to form a stream of normal olefins. Further, the method polymerizes the stream of normal olefins to form a stream of polymerized normal olefins. The method also includes saturating the stream of polymerized normal olefins to form a stream of normal paraffins.

23 Claims, 2 Drawing Sheets

(56) References Cited

U.S. PATENT DOCUMENTS

| | | |
|---|---|---|
| 4,111,791 A | 9/1978 | Davis |
| 4,422,925 A | 12/1983 | Williams et al. |
| 4,503,265 A | 3/1985 | Schleppinghoff et al. |
| 4,853,104 A | 8/1989 | Degnan, Jr. et al. |
| 5,021,143 A | 6/1991 | Franckowiak et al. |
| 5,220,102 A * | 6/1993 | Funk et al. .................. 585/829 |
| 5,382,707 A | 1/1995 | Rubin et al. |
| 5,685,972 A | 11/1997 | Timken et al. |
| 5,744,667 A * | 4/1998 | Pellet ........................... 585/257 |
| 6,657,090 B2 | 12/2003 | Rix et al. |
| 7,304,195 B2 | 12/2007 | Choi et al. |
| 7,473,812 B2 | 1/2009 | Peters et al. |
| 7,932,428 B2 | 4/2011 | Rix et al. |
| 8,115,042 B2 | 2/2012 | Godsmark et al. |
| 8,246,811 B2 | 8/2012 | Debuisschert et al. |
| 8,529,754 B2 | 9/2013 | Cui et al. |
| 2006/0264686 A1 | 11/2006 | Kerker et al. |
| 2009/0314683 A1 | 12/2009 | Matsushita |
| 2010/0056834 A1 | 3/2010 | Phillion et al. |
| 2011/0000818 A1 | 1/2011 | Xu et al. |

FOREIGN PATENT DOCUMENTS

| | | |
|---|---|---|
| WO | 2013013887 A2 | 1/2013 |
| WO | 2013013888 A2 | 1/2013 |
| WO | 2013064302 A1 | 5/2013 |

OTHER PUBLICATIONS

Butzert, H.E., et al., "A Discussion of C-4 Processing Technologies in the Eighties," Aiche 1987 Summer Natl. Meet. (Minneapolis Aug. 16-19, 1987) Prepr. N.2A 18P, Aug. 16, 1987.

Lappas, A.A, "Separation, characterization, and catalytic cracking kinetics of aromatic fractions obtained from FCC feedstocks" Applied Catalysis A: General (ISSN 0926-860X) V152 N.1 7-26 (Apr. 24, 1997), v 152, n 1, p. 7-26, Apr. 24, 1997; ISSN: 0926860X.

* cited by examiner

METHODS AND APPARATUSES FOR PROCESSING HYDROCARBONS

TECHNICAL FIELD

The technical field generally relates to apparatuses and methods for processing hydrocarbons, and more particularly relates to methods and apparatuses that convert olefins to longer chain normal paraffins.

BACKGROUND

Fluid catalytic cracking (FCC) processes convert relatively high boiling or heavy hydrocarbon fractions, such as crude oil, straight-run atmospheric gas oils, vacuum gas oils, certain atmospheric residues and heavy stocks recovered from other refinery operations, into more valuable lighter hydrocarbons, such as those in the gasoline boiling range. In a typical FCC process, a high boiling feedstock is contacted in one or more reaction zones with a particulate cracking catalyst. The reaction zones are maintained at conditions suitable for carrying out the desired cracking reactions and are free of hydrogen.

The absence of hydrogen in FCC reaction zones results in the formation of a cracked product stream with a significant quantity of aromatic and other unsaturated compounds that may be favorably blended into gasoline due to their high octane values. These gasoline boiling range hydrocarbons are normally removed as a vapor fraction from an FCC fractionation column that separates the FCC reactor effluent after exiting the reaction zone(s).

Recently, the operation of many FCC processes has focused on raising yields of light olefins, and propylene in particular, by increasing the extent of cracking or conversion. Propylene is an important raw material in many petrochemicals, and its production from sources other than FCC, such as its production as a byproduct of steam cracking, is not expected to meet the increasing demand. Typically, FCC processes operated at conditions promoting the formation of propylene also form a nearly equal amount of butenes. Conventionally, the butene produced by the FCC process is used in the production of alkylates.

Typically, the heavy naphtha produced in the FCC unit is charged to a reforming unit to produce aromatics. When operated at high severity to maximize propylene production, conventional integrated refinery and petrochemical complexes have a limited ability to manage the quantity and type of feed molecules that readily convert to aromatics during reforming.

Accordingly, it is desirable to provide methods and apparatuses for processing hydrocarbons that convert olefins to longer chain normal paraffins that may be processed to form aromatics. It is also desirable to provide methods and apparatuses for processing hydrocarbons that enable an increase in the production of aromatics from products of the FCC process. Also, it is desirable to provide such methods and apparatuses that operate economically. Furthermore, other desirable features and characteristics will become apparent from the subsequent detailed description and the appended claims, taken in conjunction with the accompanying drawings and the foregoing technical field and background.

BRIEF SUMMARY

Methods and apparatuses for processing hydrocarbons are provided. In one embodiment, a method for processing hydrocarbons includes providing a stream of olefins including normal olefins and non-normal olefins. The method includes separating the normal olefins from the non-normal olefins to form a stream of normal olefins. Further, the method polymerizes the stream of normal olefins to form a stream of polymerized normal olefins. The method also includes saturating the stream of polymerized normal olefins to form a stream of normal paraffins.

In another embodiment, a method for processing hydrocarbons includes introducing a stream of mixed C4 olefins to a reaction zone and converting a portion of the stream of mixed C4 olefins to C5 species. The method separates the C5 species from unconverted C4 olefins. Further, the method includes polymerizing the unconverted C4 olefins to form C8 olefins and saturating the C8 olefins to form C8 paraffins.

In another embodiment, an apparatus for processing hydrocarbons is provided. The apparatus includes a separation zone configured to receive a stream of olefins including normal olefins and non-normal olefins and to separate the normal olefins from the non-normal olefins to form a stream of normal olefins. Also, the apparatus includes a polymerization zone configured to polymerize the stream of normal olefins to form a stream of polymerized normal olefins. The apparatus further includes a saturation zone configured to saturate the stream of polymerized normal olefins to form a stream of normal paraffins.

BRIEF DESCRIPTION OF THE DRAWINGS

Embodiments of methods and apparatuses for processing hydrocarbons will hereinafter be described in conjunction with the following drawing figures wherein.

DETAILED DESCRIPTION

The following detailed description is merely exemplary in nature and is not intended to limit the methods or apparatuses for processing hydrocarbons. Furthermore, there is no intention to be bound by any theory presented in the preceding background or the following detailed description.

As described herein, methods and apparatuses process hydrocarbons to enhance the production of valuable product streams. For example, in an embodiment herein, olefins are converted into more valuable longer chain normal paraffins. Specifically, butenes such as those formed as byproducts during the production of propylene from a FCC unit are converted to normal paraffins, such as normal C8 and C12 paraffins. The conversion of butenes to normal paraffins includes separating normal butenes from a mix of normal and non-normal butenes, polymerizing the normal butenes to longer chain normal olefins, and saturating the longer chain normal olefins to normal paraffins. Further processing may be performed to reform the normal paraffins to produce aromatics.

Figure 1:
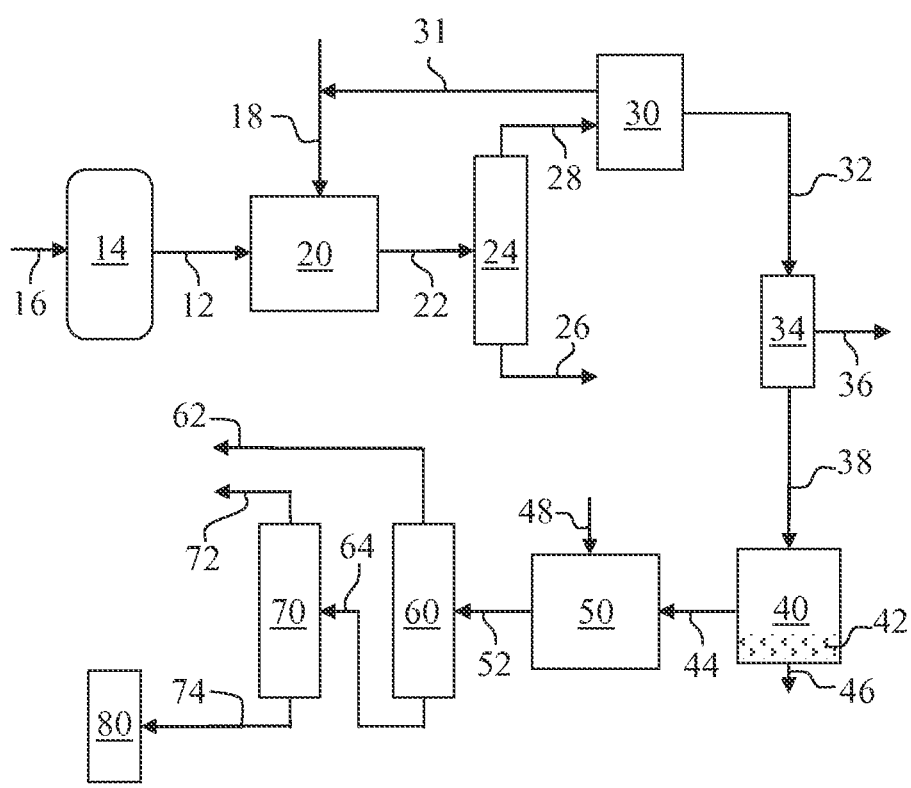
FIG. 1 is a schematic diagram of an apparatus and method for processing hydrocarbons in accordance with an embodiment herein.

Referring to FIG. 1, an exemplary apparatus 10 is provided for processing hydrocarbons. As shown, a feed stream 12 is fed to the apparatus 10. An exemplary feed stream 12 includes olefins formed by an upstream processing unit 14, such as an FCC reactor. For example, the feed stream 12 may be a mixed stream of butenes formed as a byproduct of an FCC process for forming propylene. High severity FCC processing converts a feedstock 16 of relatively high boiling or heavy hydrocarbon fractions, such as crude oil, straight-run atmospheric gas oils, vacuum gas oils, certain atmospheric residues and heavy stocks recovered from other refinery operations and forms a propylene stream (not shown) as well as the feed stream 12, which is a mix of C4 butene isomers including 1-butene, cis-2-butene, trans-2-butene, and 2-methylpropene (conventionally referred to as isobutylene or isobutene). 1-Butene, cis-2-butene, and trans-2-butene are normal olefins, while isobutene is a branched, or non-normal, olefin. High severity FCC processing conditions include a temperature of from about 540° C. to about 580° C., for example from about 550° C. to about 580° C., and a gauge pressure of from about 100 kiloPascals (kPa) to 300 kPa (about 1 bar to about 3 bar), for example about 70 kPa to about 140 kPa (about 0.7 bar to about 1.4 bar).

An exemplary embodiment of the apparatus 10 converts the feed stream 12 to a more valuable longer chain normal paraffin stream, by first separating and removing the non-normal portion of the feed stream 12. As shown, the feed stream 12 and a stream 18 of methanol are fed to a non-normal conversion reaction zone 20, such as a reactor column. The feed stream 12 may first be washed with water to remove catalyst poisons such as nitrogen compounds and metal ions. The feed stream 12 and methanol stream 18 are mixed and contacted with an etherification catalyst such as an acid ion exchange resin in the non-normal conversion reaction zone 20 such that the non-normal portion, e.g., the isobutene, in the exemplary feed stream 12 selectively reacts to form a C5 species, such as methyl tertiary butyl ether (MTBE), in a reaction effluent 22.

The reaction forming MTBE is exothermic and the reactor effluent 22 has a higher temperature than the feed stream 12 entering the non-normal conversion reaction zone 20. Therefore, while not shown, the reactor effluent 22 may be heat exchanged with the feed stream 12 to increase the temperature of the feed stream 12 before entering the non-normal conversion reaction zone 20. In an exemplary embodiment, the feed stream 12 enters the non-normal conversion reaction zone 20 at a temperature of about 60° C. to about 120° C., such as about 80° C. to about 90° C.

In the exemplary embodiment, after exiting the non-normal conversion reaction zone 20, the reaction effluent 22 is fed to a separator 24, for example a distillation column. The separator 24 separates the MTBE in an extract stream 26 from the methanol and the unconverted butenes that remain in a raffinate stream 28. The MTBE in the extract stream 26 may be sent to gasoline blending, such as for use as an oxygenate to provide an increased octane number.

As shown in FIG. 1, the raffinate stream 28 is introduced to a methanol recovery unit 30 that separates methanol from the unconverted butenes. For example, the methanol recovery unit 30 may wash the raffinate stream 28 with water to remove the methanol therefrom. In the exemplary process, the methanol is separated from the wash water and is recycled as methanol stream 31 to the stream 18 of methanol fed to the non-normal conversion reaction zone 20.

Removal of the methanol from the raffinate stream 28 results in the formation of a normal olefin stream 32. An exemplary normal olefin stream 32 includes 1-butene, cis-2-butene, and trans-2-butene. As described, the normal olefin stream 32 is formed by separating and removing the non-normal portion of the feed stream 12, e.g., the isobutene. Thus, the non-normal conversion reaction zone 20, separator 24, and methanol recovery unit 30 may be considered to form a separation zone for forming the normal olefin stream 32.

In the exemplary embodiment, the normal olefin stream 32 exits the methanol recovery unit 30 of the separation zone and is fed to a pretreatment unit 34. The exemplary pretreatment unit 34 removes contaminants 36 from the normal olefin stream 32, such as trace oxygenates, diolefins, and water. After the contaminants 36 are removed, the normal olefin stream 38 exits the pretreatment unit 34.

In the exemplary embodiment, the normal olefin stream 38 is fed to a polymerization reaction zone 40. The exemplary polymerization reaction zone 40 holds a catalyst 42 that supports polymerization of the olefins in the normal olefin stream 38. An exemplary catalyst 42 is a solid zeolitic catalyst. In an exemplary embodiment, the catalyst 42 is of the type ZSM-Twenty-Three, conventionally referred to as the type MTT. For example, the catalyst may have the element system and formula of:

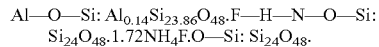

$$\text{Si}_{24}\text{O}_{48} \cdot 1.72\text{NH}_4\text{F} \cdot \text{O}\text{—Si: Si}_{24}\text{O}_{48}.$$

In the polymerization reaction zone 40, butenes in the normal olefin stream 38 are polymerized to form longer straight chain olefins. Specifically, the butenes are polymerized to form normal octenes (straight chain C8s having a double bond) and normal dodecenes (straight chain C12s having a double bond), as well as some heavier olefins. In an exemplary embodiment, the polymerization reaction zone 40 polymerizes at least about 50 weight percent (wt %) of the normal olefins in the normal olefin stream 38, such as about 75 wt % of the normal olefins in the normal olefin stream 38. Further, in an exemplary embodiment, at least about 50 wt % of the butenes in the normal olefin stream 38 are converted into octenes. In an exemplary embodiment, at least about 10 wt % of the butenes in the normal olefin stream 38 are converted into dodecenes. An olefin stream 44 including octenes, dodecenes, heavier olefins, and unreacted butenes exits the polymerization reaction zone 40. As shown, unreacted paraffins 46 present in feed stream 12 are also removed from the polymerization reaction zone 40.

As shown, the olefin stream 44 and a hydrogen stream 48 are fed to a saturation zone 50. An exemplary saturation zone 50 contains a saturation or hydrogenation catalyst that catalyzes a hydrogenation reaction to convert the olefins to paraffins. For example, in an exemplary hydrogenation reaction octene is saturated to form octane and dodecene is saturated to form dodecane. Any non-polymerized C4 olefins may be saturated to form C4 paraffins. Longer chain olefins are also saturated to form longer chain paraffins. The saturation catalyst may be any suitable catalyst supporting the hydrogenation of olefins to paraffins, such as a metal catalyst like platinum, palladium, rhodium, or ruthenium bound on a support. The saturation zone 50 is maintained at conditions conducive to maximize the formation of paraffins such as at a temperature of from about 200° C. to about 300° C.

A paraffin stream 52 is formed within the saturation zone 50 and is minimally branched. Specifically, the paraffin stream 52 includes at least about 75 wt % normal compounds, for example, at least about 90 wt % normal compounds. As shown, the paraffin stream 52 is fed to a product recovery zone. Specifically, the paraffin stream 52 is introduced to a first fractionation column 60 that removes a stream 62, such as exemplary overhead stream 62, including C3 hydrocarbons and any lighter compounds, i.e., components having lower boiling temperatures. A stream 64, such as exemplary bottom stream 64, is formed by the first fractionation column 60 and includes C4 hydrocarbons and heavier compounds, i.e., compounds having higher boiling temperatures. The bottom stream 64 is fed to a second fractionation column 70 where it is fractionated into a stream 72, such as exemplary overhead stream 72, including C4 paraffins, and a product paraffins stream 74, such as exemplary bottom product paraffin stream 74, including a saturated gasoline product containing normal paraffin compounds heavier than C4 paraffins, such as octanes and dodecanes.

The product paraffin stream 74 includes longer chain normal paraffins relative to the olefins in the feed stream 12 that enable an increase in the production of aromatics from the feed stream 12. To form aromatics from the paraffins in the product paraffin stream 74, the product paraffin stream 74 is fed to a reforming zone 80.

Figure 2:
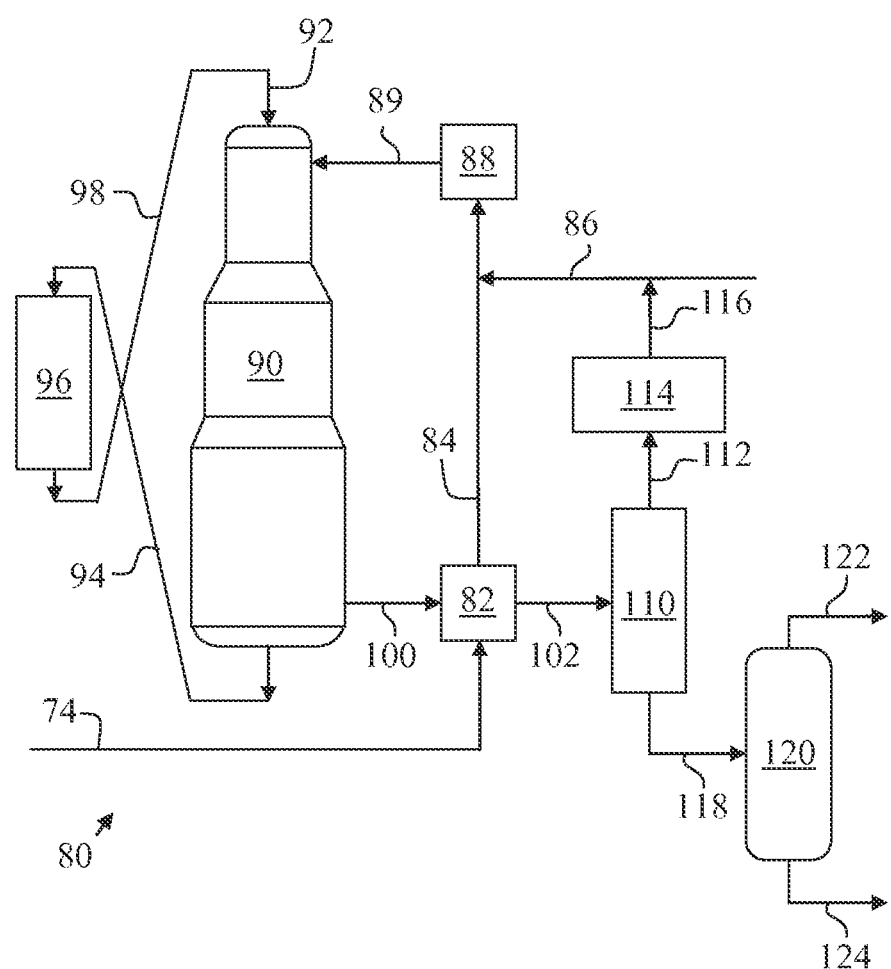
FIG. 2 is a schematic diagram of the reforming zone of FIG. 1.

As shown in FIG. 2, an exemplary reforming zone 80 for use in the apparatus 10 of FIG. 1 receives the product paraffin stream 74 containing normal paraffins and heats the product paraffin stream 74 via a heat exchanger 82 to form heated product stream 84. Hydrogen 86 is added to the heated product stream 84. While the exemplary embodiment adds the hydrogen 86 to the product stream 84 downstream of the heat exchanger 82, the hydrogen 86 may be added to the product paraffin stream 74 upstream of the heat exchanger 82. The product stream 84 may be further heated in a heater 88 to provide the product stream 89 with a desired temperature for introduction to a reforming zone 90, such as a reforming reactor or reactors. For example, the product stream 89 may have a temperature of about 500° C. to about 550° C., such as about 520° C. to about 540° C.

In the exemplary embodiment of FIG. 2, the reforming zone 90 continuously receives a stream of catalyst 92, though alternatively the reforming zone 90 may hold catalyst that is removed and replaced offline. In either case, the normal paraffins in the product paraffin stream 74 undergo catalytic conversion in the presence of the hydrogen to form aromatics in the reforming zone 90. Specifically, the paraffins undergo dehydrocyclization, including dehydrogenation and aromatization, to form aromatics such as xylene.

Exemplary catalysts supporting dehydrocyclization in the reforming zone 90 include Group VIII metals and medium pore non-zeolitic molecular sieves. As shown, spent catalyst 94 exits the reforming zone 90 and is regenerated in a regeneration zone 96. Regenerated catalyst 98 is then fed back to the reforming zone 90 as catalyst 92.

A reforming effluent 100 also exits the reforming zone 90. The reforming effluent 100 is passed through heat exchanger 82 to heat the incoming product paraffin stream 74. The cooled reforming effluent 102 is then fed to a gas separator 110 where hydrogen 112 is removed from the reforming effluent 102. The hydrogen 112 may be compressed in a compressor 114 and fed in stream 116 to the hydrogen 86 for re-introduction into the product stream 84.

As shown, the gas separator 110 separates a liquid stream 118 from the reforming effluent 102. The liquid stream 118 is introduced to a stabilizer unit 120. Stabilizer unit 120 forms an overhead stream 122 including lighter weight compounds, such as C4 hydrocarbons and compounds lighter than C4 hydrocarbons. Further, the stabilizer unit 120 forms a liquid reformate 124. An exemplary liquid reformate 124 includes at least about 50% aromatics, for example at least about 75% aromatics.

FIG. 3 illustrates an alternate embodiment of the apparatus 10 of FIG. 1. In FIG. 3, the apparatus includes the separator 24 that separates the MTBE in an extract stream 26 from the methanol and the unconverted butenes that remain in a raffinate stream 28. The MTBE in the extract stream 26 is fed to a decomposition unit 150 to convert the MTBE into isobutene. The decomposition unit 150 may be, for example, a membrane reactor in which the MTBE is decomposed into isobutene and methanol, and in which isobutene and methanol are separated from one another. An exemplary decomposition unit 150 includes a decomposition catalyst, such as a heteropoly acid catalyst. In the decomposition unit 150, the extract stream 26 of MTBE is decomposed over the catalyst to form high purity isobutene, such as having an isobutene content of at least about 97 wt %, and high purity methanol, such as having a methanol content of at least about 97 wt %. The stream 152 of isobutene exits the decomposition unit 150 and is fed back into the feedstock 16 for introduction into the upstream processing unit 14. An FCC unit operating as the upstream processing unit 14 may increase its propylene production incrementally by recycling the stream 152 back into feedstock 16. As shown, the stream 154 of methanol exits the decomposition unit 150 and is fed into the stream 18 of methanol entering the non-normal conversion reaction zone 20.

As described herein, a method and apparatus for processing hydrocarbons have been provided. Specifically, a method and apparatus has been provided for the conversion of butenes into longer chain normal paraffins. Such paraffins may be further converted into aromatics. In such case, a method and apparatus is provided for converting butenes into aromatics. The method and apparatus described above are particularly well-suited for the processing of butenes created as a byproduct of an FCC process for forming propylene and to form aromatics for gasoline blending from the butenes.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the claimed subject matter in any way. Rather, the foregoing detailed description will provide those skilled in the art with a convenient road map for implementing an exemplary embodiment or embodiments. It being understood that various changes may be made in the function and arrangement of elements described in an exemplary embodiment without departing from the scope set forth in the appended claims.

What is claimed is:

1. A method for processing hydrocarbons, the method comprising the steps of:
    providing a stream of olefins including normal olefins and non-normal olefins;
    separating the normal olefins from the non-normal olefins to form a stream of normal olefins;
    polymerizing the stream of normal olefins to form a stream of polymerized normal olefins;
    saturating the stream of polymerized normal olefins to form a stream of normal paraffins; and
    reforming the stream of normal paraffins to form a stream of aromatics.

2. The method of claim 1 wherein saturating the stream of polymerized normal olefins to form a stream of normal paraffins comprises forming the stream of normal paraffins comprising at least about 75 wt % normal compounds.

3. The method of claim 1 wherein saturating the stream of polymerized normal olefins to form a stream of normal paraffins comprises forming the stream of normal paraffins comprising at least about 90 wt % normal compounds.

4. The method of claim 1 wherein polymerizing the stream of normal olefins to form a stream of polymerized normal olefins comprises polymerizing at least about 50 wt % of the normal olefins.

5. The method of claim 1 wherein polymerizing the stream of normal olefins to form a stream of polymerized normal olefins comprises polymerizing at least about 75 wt % of the normal olefins.

6. The method of claim 1 wherein providing a stream of olefins including normal olefins and non-normal olefins comprises providing a stream of mixed C4 olefins, and wherein separating the normal olefins from the non-normal olefins to form a stream of normal olefins comprises:
converting a portion of the stream of mixed C4 olefins to a C5 species; and
separating the C5 species from unconverted C4 olefins.

7. The method of claim 1 wherein providing a stream of olefins including normal olefins and non-normal olefins comprises providing a stream of mixed C4 olefins, and wherein separating the normal olefins from the non-normal olefins to form a stream of normal olefins comprises:
converting isobutene to methyl tertiary butyl ether (MTBE); and
separating the MTBE from unconverted C4 olefins.

8. The method of claim 1 wherein:
providing a stream of olefins including normal olefins and non-normal olefins comprises providing a stream of mixed C4 olefins; and
polymerizing the stream of normal olefins to form a stream of polymerized normal olefins comprises forming the stream of polymerized normal olefins comprising at least about 50 wt % normal octene.

9. The method of claim 1 wherein:
providing a stream of olefins including normal olefins and non-normal olefins comprises providing a stream of mixed C4 olefins; and
polymerizing the stream of normal olefins to form a stream of polymerized normal olefins comprises forming the stream of polymerized normal olefins comprising at least about 50 wt % normal octene and at least about 10 wt % normal dodecene.

10. A method for processing hydrocarbons, the method comprising the steps of:
introducing a stream of mixed C4 olefins to a reaction zone;
converting a portion of the stream of mixed C4 olefins to a C5 species;
separating the C5 species from unconverted C4 olefins;
polymerizing the unconverted C4 olefins to form C8 olefins; and
saturating the C8 olefins to form C8 paraffins.

11. The method of claim 10 further comprising reforming the C8 paraffins to form aromatics.

12. The method claim 10 wherein converting a portion of the stream of mixed C4 olefins to a C5 species comprises converting isobutene to methyl tertiary butyl ether (MTBE).

13. The method of claim 10 wherein saturating the C8 olefins to form C8 paraffins comprises saturating non-polymerized C4 olefins to form C4 paraffins.

14. The method of claim 10 wherein:
separating the C5 species from unconverted C4 olefins comprises forming a stream of normal C4 olefins;
polymerizing the unconverted C4 olefins to form C8 olefins comprises forming normal C8 olefins; and
saturating the C8 olefins to form C8 paraffins comprises forming normal C8 paraffins.

15. The method of claim 10 wherein polymerizing the unconverted C4 olefins to form C8 olefins comprises polymerizing at least about 50 wt % of the unconverted C4 olefins into C8 olefins.

16. The method of claim 15 wherein polymerizing the unconverted C4 olefins to form C8 olefins comprises polymerizing at least about 10 wt % of the unconverted C4 olefins into C12 olefins.

17. The method of claim 10 wherein:
separating the C5 species from unconverted C4 olefins comprises forming a stream of normal C4 olefins;
polymerizing the unconverted C4 olefins to form C8 olefins comprises forming a stream of polymerized olefins; and
saturating the C8 olefins to form C8 paraffins comprises saturating the stream of polymerized olefins to form a stream of saturated paraffins comprising at least about 75 wt % normal compounds.

18. The method of claim 10 wherein:
separating the C5 species from unconverted C4 olefins comprises forming a stream of normal C4 olefins;
polymerizing the unconverted C4 olefins to form C8 olefins comprises forming a stream of polymerized olefins; and
saturating the C8 olefins to form C8 paraffins comprises saturating the stream of polymerized olefins to form a stream of saturated paraffins comprising at least about 90 wt % normal compounds.

19. An apparatus for processing hydrocarbons comprising:
a separation zone configured to receive a stream of olefins including normal olefins and non-normal olefins and to separate the normal olefins from the non-normal olefins to form a stream of normal olefins;
a polymerization zone configured to polymerize the stream of normal olefins to form a stream of polymerized normal olefins; and
a saturation zone configured to saturate the stream of polymerized normal olefins to form a stream of normal paraffins.

20. A method for processing hydrocarbons, the method comprising the steps of:
providing a stream of mixed C4 olefins including normal olefins and non-normal olefins;
separating the normal olefins from the non-normal olefins to form a stream of normal olefins by converting a portion of the stream of mixed C4 olefins to a C5 species; and separating the C5 species from unconverted C4 olefins;
polymerizing the stream of normal olefins to form a stream of polymerized normal olefins; and
saturating the stream of polymerized normal olefins to form a stream of normal paraffins.

21. A method for processing hydrocarbons, the method comprising the steps of:
providing a stream of mixed C4 olefins including normal olefins and non-normal olefins;
separating the normal olefins from the non-normal olefins to form a stream of normal olefins by converting isobutene to methyl tertiary butyl ether (MTBE) and separating the MTBE from unconverted C4 olefins;
polymerizing the stream of normal olefins to form a stream of polymerized normal olefins; and
saturating the stream of polymerized normal olefins to form a stream of normal paraffins.

22. A method for processing hydrocarbons, the method comprising the steps of:
providing a stream of mixed C4 olefins including normal olefins and non-normal olefins;
separating the normal olefins from the non-normal olefins to form a stream of normal olefins;
polymerizing the stream of normal olefins to form a stream of polymerized normal olefins comprising at least about 50 wt % normal octene; and
saturating the stream of polymerized normal olefins to form a stream of normal paraffins.

23. A method for processing hydrocarbons, the method comprising the steps of:

providing a stream of mixed C4 olefins including normal olefins and non-normal olefins;

separating the normal olefins from the non-normal olefins to form a stream of normal olefins;

polymerizing the stream of normal olefins to form a stream of polymerized normal olefins comprising at least about 50 wt % normal octene and at least about 10 wt % normal dodecene; and saturating the stream of polymerized normal olefins to form a stream of normal paraffins.

* * * * *